United States Patent
Power

(10) Patent No.: US 6,210,431 B1
(45) Date of Patent: Apr. 3, 2001

(54) OSTIAL BIFURCATION LESION STENTING CATHETER

(76) Inventor: John A. Power, 202 Springhouse La., Pittsburgh, PA (US) 15238

(*) Notice: Subject to any disclaimer, the term of this patent is extended or adjusted under 35 U.S.C. 154(b) by 0 days.

(21) Appl. No.: 09/458,783

(22) Filed: Dec. 10, 1999

(51) Int. Cl.⁷ ............................................. A61M 29/00
(52) U.S. Cl. ........................................ 623/1.11; 606/198
(58) Field of Search ................................. 623/1.11, 1.23, 623/1.35, 1.37; 606/108, 194, 191, 198, 192, 195

(56) References Cited

U.S. PATENT DOCUMENTS

| | | |
|---|---|---|
| 4,681,110 | 7/1987 | Wiktor . |
| 4,886,062 | 12/1989 | Wiktor . |
| 4,913,142 | 4/1990 | Kittrell . |
| 4,969,458 | 11/1990 | Wiktor . |
| 5,133,732 | 7/1992 | Wiktor . |
| 5,217,454 | 6/1993 | Khoury . |
| 5,437,659 | 8/1995 | Leckbone . |
| 5,575,816 | 11/1996 | Rudnick . |
| 5,591,228 * | 1/1997 | Edoga ........................................ 623/1 |
| 5,632,762 * | 5/1997 | Myler ...................................... 606/194 |
| 5,669,932 | 9/1997 | Fischell . |
| 5,722,972 | 3/1998 | Power . |
| 5,749,890 * | 5/1998 | Shaknovich ........................ 606/198 |

* cited by examiner

Primary Examiner—Michael Buiz
Assistant Examiner—Vy Q. Bui
(74) Attorney, Agent, or Firm—Clifford A. Poff

(57) ABSTRACT

A stent deploying catheter and method for placing a stent in a branching anatomic duct commencing at the ostium includes a distal portion containing a forward facing abutment surface laterally offset from a proximal end of a forward extending stent carrier. The forward facing abutment surface overlies the radio opaque marker to aid in the orientation and placement of the stent. The forwarding extending stent carrier in one embodiment includes a catheter balloon and having a length sufficient for supporting and deploying a stent to treat an ostial bifurcation lesion. The stent carrier in another embodiment includes a sheathing which can be retracted for deploying a self-expanding stent. An actuator wire extends along the catheter for angularly displacing the distal end portion in a body vessel to align the abutment surface with a common vessel wall at the crux of a vessel bifurcation and align the stent carrier along the site of the ostial bifurcation lesion. A guide wire lumen is also provided for the introduction and guiding of the distal end portion along the vessel.

16 Claims, 6 Drawing Sheets

OSTIAL BIFURCATION LESION STENTING CATHETER

BACKGROUND OF THE INVENTION

1. Field of the Invention

The present invention relates to a stenting catheter for transporting and deploying a stent in a branching anatomic duct having a stenosis attributed to a lesion commencing at the ostium, or entrance, of the branching duct and more particularly to such a catheter having a distal end portion including a forward facing abutment surface laterally offset from a proximal end of a forward extending stent carrier controllably positioned to align the abutment surface with the crux of the branching anatomic duct.

2. Description of the Prior Art

Angioplasty is a procedure involving the use of a balloon-tipped catheter to treat a narrowed anatomic duct such as a coronary artery. The catheter is used to advance the balloon mounted on the distal end of a catheter within the narrowed opening and then expand the balloon one or more times to compress arterial plaque and enlarge the narrowed opening. Anatomic ducts treated by angioplasty however can re-close within a short time (referred to as acute re-closure) or again assume a re-narrowing over extended time period (referred to as re-stenosis).

Stenting is a technique used to open blocked arteries in patients who have atherosclerosis. The blocked arteries can affect any organ system in the body but are most frequently approached with stenting when the lesion or blockage affects an artery supplying fluid to the heart, brain, kidney or legs.

The installation of a stent initially involves the same angioplasty procedure of placing a guide-wire across the blockage in the artery and then advancing a balloon dilatation catheter along the guide-wire to the site of the blockage whereupon the balloon is inflated to compress plaque and dilate the blockage. A selected stent arranged on a dilation balloon is advanced along the artery with the aid of the guide wire to position the stent along the site of the blockage. The balloon is inflated to permanently enlarge the stent against the wall of the artery leaving the stent anchored in place after deflating the balloon and removal of the catheter and guide wire. The stent serves as a prop in the artery to help prevent both acute re-closure and re-stenosis and also serves to maintain dilation of the vessel to prevent the treated area of the blood vessel from re-stenosis.

Treating a lesion with a stent in a branching anatomic duct represents a prevalent and a particularly difficult geometry to achieve placement of a stent at the exact location of atherosclerotic blockage. FIG. 1 illustrates an example of a branching anatomic duct 10 with atherosclerotic plaque 14 at the ostium 16 of a side branch duct 18 of a main duct 20. The side branch and the main branch form an angled relationship identified as angle β which can be a right angle but usually an acute angle. FIG. 2 illustrates an example of improper longitudinal positioning of an end of the stent which as is well known cannot be corrected after deployment of the stent. A residual of treated atherosclerotic plaque 14A at the ostium 16 of a side branch duct 18 remains after the deployment of a stent 22. The protruding end 22A of the stent 22 extending from the ostium 16 into the main duct 20 becomes a partial obstruction that impedes the flow in both the branching duct 18 and the main duct 20. FIG. 3 illustrates a misplacement of stent 22 too deeply in the side branch 18 thereby leaving a residual of untreated atherosclerotic plaque 14B remaining as a blockage at the ostium 16 of the side branch thereby blocking flow into the branching duct. FIG. 4 illustrates a sub optimal placement of a stent in a branching duct where an arcuate segment 22B of the stent 22 overhangs the ostium 16 at crux 16A becomes a flow impeding partial obstruction. A residual of untreated plaque 14B remains immediately adjacent to ostium 16 also becomes a flow impeding partial obstruction.

It is an object of the present invention to provide a stent delivery catheter for placing a stent to a branching anatomic duct in a controllable position using the crux of the branching anatomic duct as a reference site.

It is another of the present invention to provide a catheter to rotatably position a stent carried thereby in a duct to orientate the stent at one lateral side of a duct for controllably positioning in a branching duct at a predetermined site.

SUMMARY OF THE INVENTION

According to the present invention there is provided a stent deployment catheter having a distal portion containing a forward facing abutment surface laterally offset from a proximal end of a forward extending stent carrier having a length sufficient for supporting and deploying a stent to treat an ostial bifurcation lesion, the stent deployment catheter further having an actuator for angularly displacing the distal end portion in a body vessel to align the abutment surface with a common vessel wall at the crux of a vessel bifurcation and align the stent carrier along the site of the ostial bifurcation lesion.

According to the present invention there is also provided a method for treating an ostial bifurcation lesion, the method including the steps of advancing a stent laden carrier extending from a distal end portion of a catheter along a body vessel to a site of an ostial bifurcation lesion, angularly displacing the stent-laden carrier to orientate a stent carried thereby into a predetermined relation with the ostial bifurcation lesion established by concurrently bringing a forward facing abutment surface on the distal end portion of the catheter into a confronting relation with the crux of a vessel bifurcation at the site of the ostial bifurcation lesion, and deploying the stent from the stent-laden carrier.

BRIEF DESCRIPTION OF THE SEVERAL VIEWS OF THE DRAWINGS

These features and advantages of the present as well as others will be more fully understood when the following description is read in light of the accompanying drawings in which.

DETAILED DESCRIPTION OF THE PREFERRED EMBODIMENTS

Figure 5:
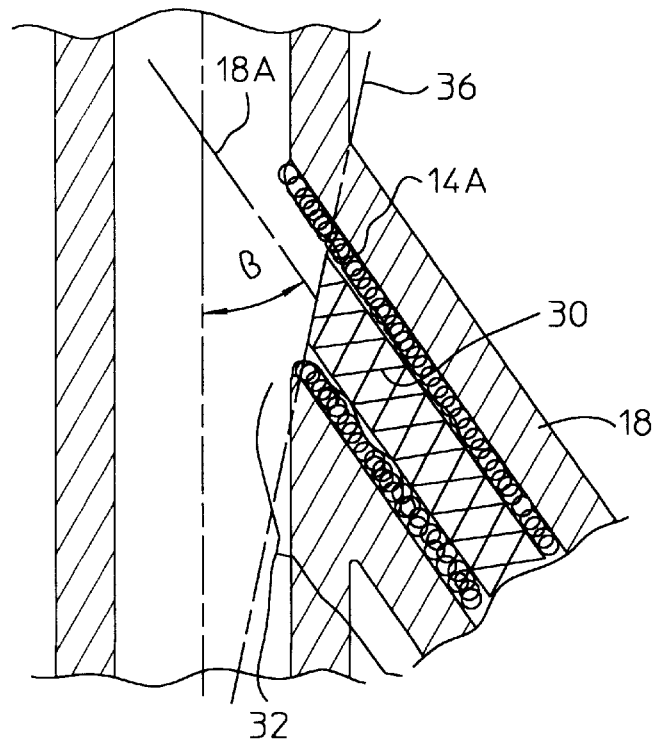
FIG. 5 illustrates an optimal placement of a stent in a branching vessel according to the present invention.

An ostial bifurcation lesion stenting catheter according to the present invention provides for an ideal placement of a stent 30 in a bifurcation duct as illustrated in FIG. 5. The stent 30 embodies a construction characterized a cylindrical body 32 formed of generally continuous wire having a deformable pattern such as zig-zag configuration as disclosed in U.S. Pat. Nos. 5,133,732 and 4,886,062 or coiled convolutions joined by versing turn as disclosed in U.S. Pat. No. 4,969,458. Other well known configurations of stent bodies are equally useful according to the present invention. A characteristic feature of the stent 30 is a beveled terminal end 34 of the stent body generally lying in a plane 36 forming biased relation with the extended length of the stent body. The plane 36 is generally parallel with the longitudinal central axis of the main duct 20 and forms an angle β with the longitudinal central axis 18A of side branch duct 18. The remaining terminal end configuration of the stent body can be any desired configuration typically terminating in a plane perpendicular to the extended length of the stent body 30. The correct placement of the stent 30 insures a generally a residue of treated atherosclerotic plaque 14A with the beveled end 32 of stent 30 located proximate to the ostium 16 defining the entrance into the side branch 18. The stent catheter of the present invention provides for angularly orientating the stent 30 such that the plane 36 of the beveled terminal end 34 forms a peripheral boarder to the ostium 16 without an overhanging of the stent 30 into the main duct 20.

Figure 1:
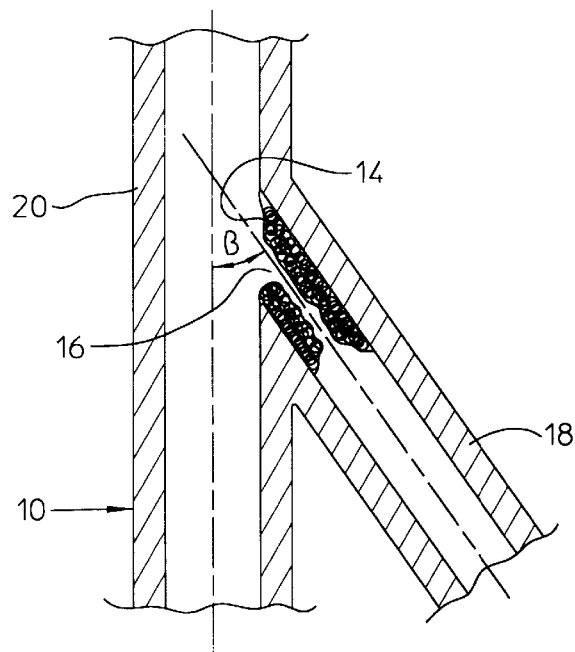
FIG. 1 illustrates an example of lesions forming blockages at a branch point of a blood vessel.
Figure 2:
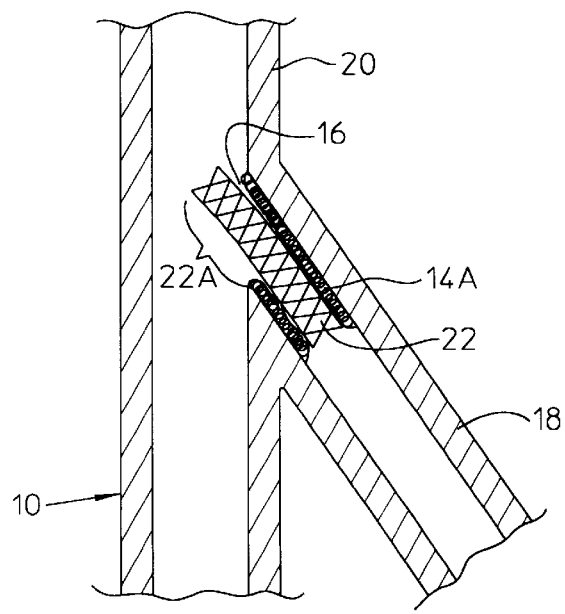
FIG. 2 illustrates one example of a misplacement of a stent in a branching vessel.
Figure 3:
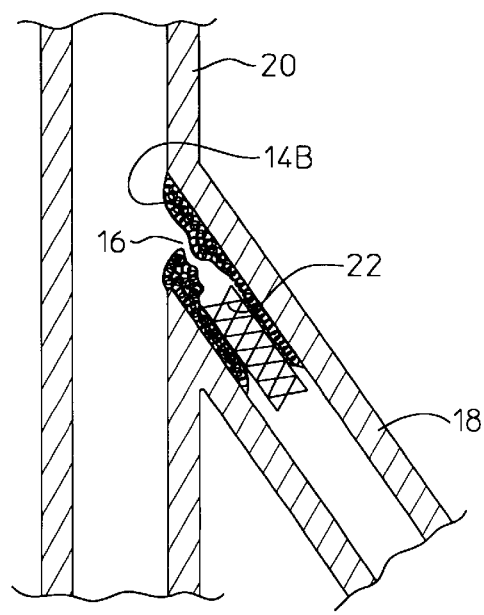
FIG. 3 illustrates another example of a misplacement of a stent in a branching vessel.
Figure 4:
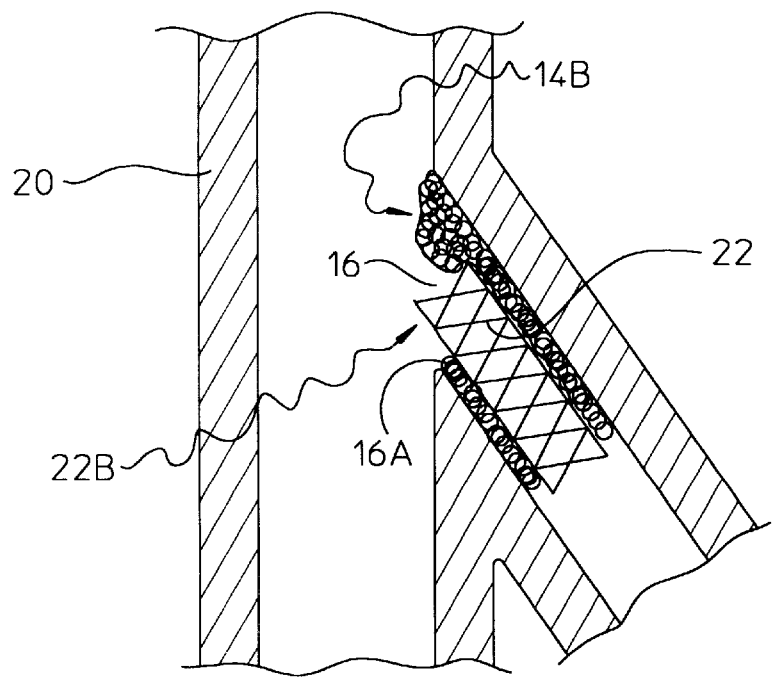
FIG. 4 illustrates a sub-optimal placement of a stent in a branching vessel.
Figure 5D:
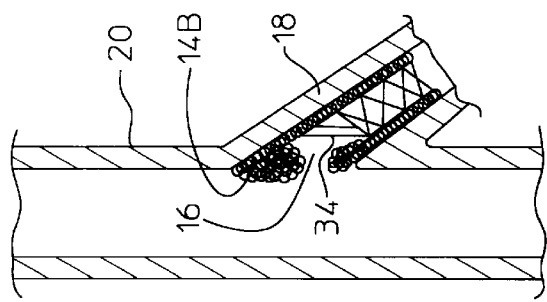
FIGS. 5A–5D illustrates a sequence of misplacements of an sent in a branching duct which can be obviated by the use of senting catheter of the present invention.
Figure 5C:
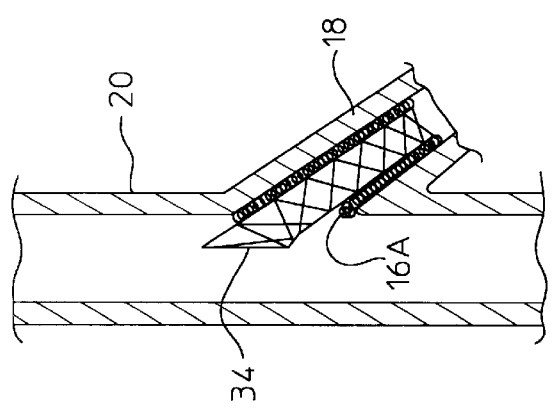
Figure 5B:
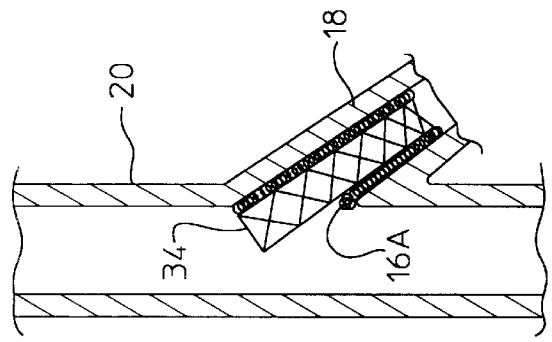
Figure 5A:
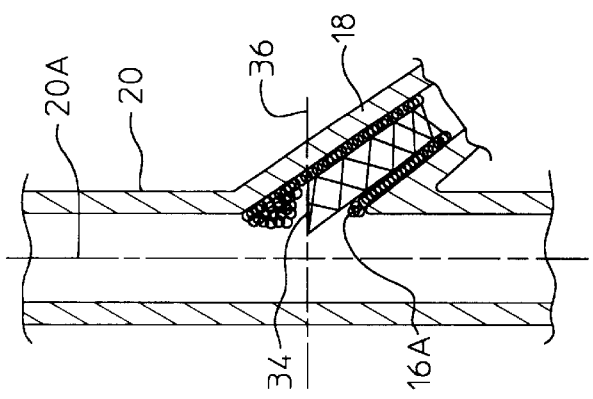

In order to fully appreciate the benefits arising out of the feature of the stenting catheter enabling orientation of a beveled end of a stent during the placement procedure, there is illustrated in FIGS. 5A–5D placement errors likely to occur without the use of a stenting catheter of the present invention. In FIG. 5A, the plane 36 of the beveled end 34 is perpendicular to the longitudinal axis 20A of the main duct and thus a 180° from the proper position. The placement error increases the detriment to that described and shown in FIG. 4 by the increase to the protruding end portion of the stent in the main duct 18. In FIG. 5B the plane 36 of the beveled end 34 is 90° from the proper position. Similar to the condition of FIG. 5A, this placement error increases the detriment to that described and shown in FIG. 4 by the increase to the protruding end portion of the stent in the main duct 20. In FIG. 5C, the plane 36 of the beveled end 34 is generally parallel to the longitudinal axis 20A of the main duct a portion of the stent at the beveled end is exteriorly situated from the branching duct line beyond the ostium in the main duct 20. The placement error increases the volume of the stent residing in duct 20 and therefor also increases the detriment to that described and shown in FIGS. 5A and 5B. In FIG. 5D stenting is in effective due to the placement of the stent too distant from the ostium 16. The plane 36 of the beveled end 34, while parallel to the longitudinal axis 20A of the main duct, the plane is distantly spaced with the resulting shortcomings described previously with regard to FIG. 3.

Figure 6:
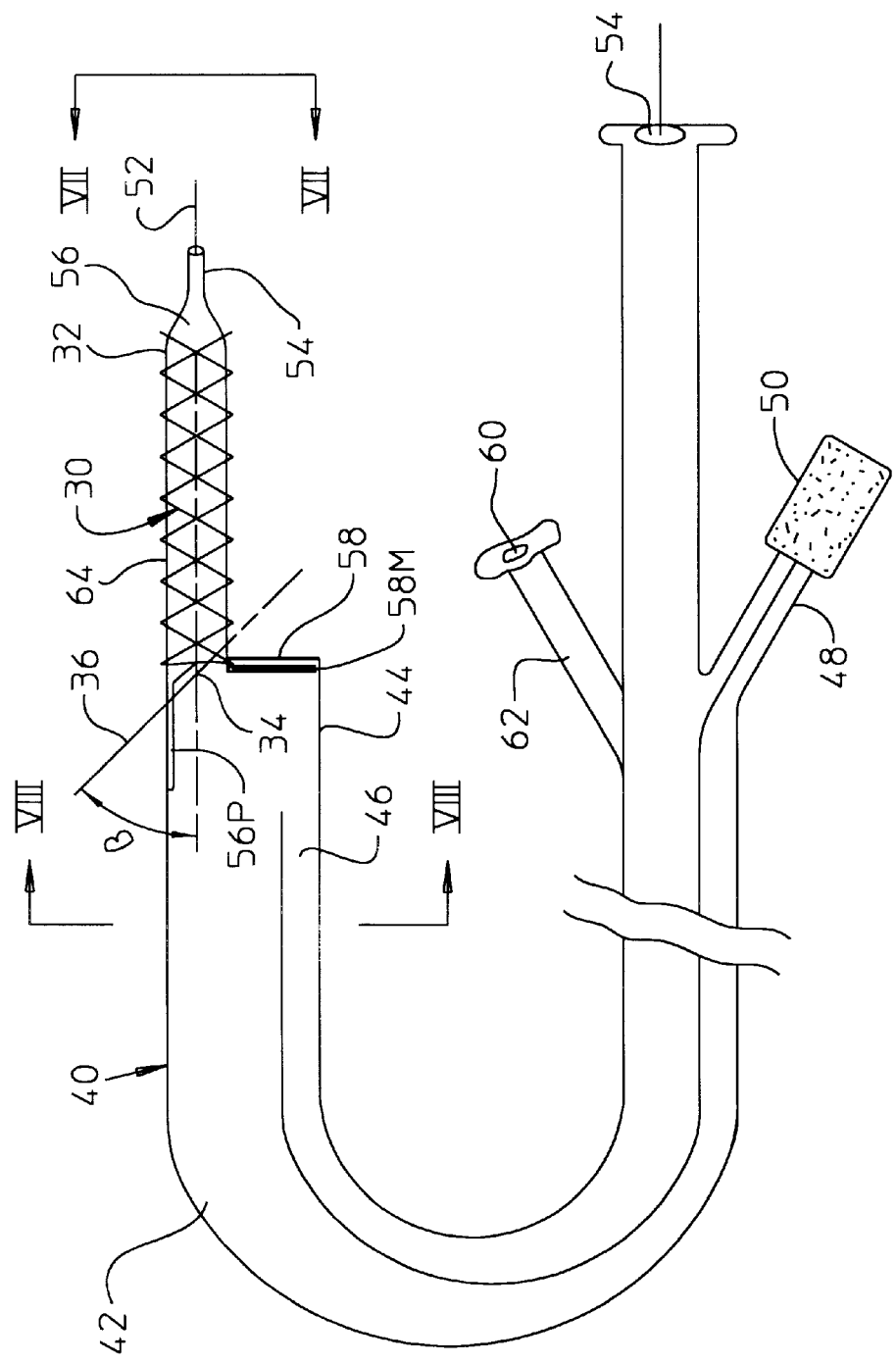
FIG. 6 is a view of a stenting catheter according to the present invention.

A ostial bifurcation lesion stenting catheter 40 according to one embodiment of the present invention is shown in FIG. 6. The catheter 40 includes an elongated main body portion 42 terminating at a distal end portion 44 having a torque transmitting wire 46 embedded therein. The wire extends to the proximal end of the catheter 40 where a port 48 takes the form of a branch duct to support a control knob 50 for applying a twisting torque to rotate the wire 46 about an axis extending along the extended length of the wire which in turn serves to rotate the distal end portion 44. A steerable guide wire 52 previously introduced to the branching anatomic duct 10 establishes a course of travel for the catheter 40 and for this purpose the catheter is provided with a guide wire lumen 54. The guide wire lumen extends through a stent carrier 56 having the form of an elongated extension with a proximal end of the stent carrier extending from the distal end portion 44. The stent carrier includes a prolongation surface 56P occurring at the proximal end of the stent carrier 56 and projecting along the distal end portion 44 in a direction toward the proximal end of the catheter 40. Thus, it can be seen that the guide wire lumen opens out of the distal end of the stent carrier. In the embodiment shown in FIG. 6, the stent carrier 56 is eccentrically situated at one later side of the distal end portion to thereby provide a step off 58 having the preferable for of a generally planar surface forming part of the terminal end face of the distal end portion. A radio opaque marker 58M is embedded in the catheter material beneath the surface of the step off 58. The step off 58 is used according to the present invention to abut the crux of a branching duct and the radio opaque marker is used to facilitate the establishment of the abutting relationship. The catheter 40 further includes a balloon inflation lumen 60 extending from a balloon inflation port 62 to a catheter balloon 64 mounted on the external face of the stent carrier 56. The stent 30 is mounted on the catheter balloon and orientated with such that the plane 36 of the beveled end forms an angle β with a longitudinal axis extending along the length of the stent which also corresponds to the longitudinal axis of the guide wire when residing in the side branch duct to receive the stent.

Figure 9D:
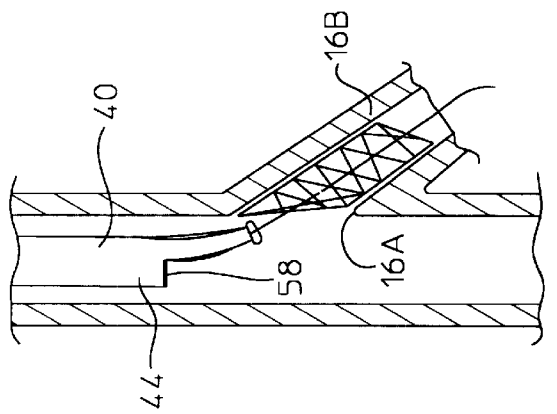
FIGS. 9A–9D illustrate a sequence for the placement of a stent using the catheter of FIG. 6.
Figure 9C:
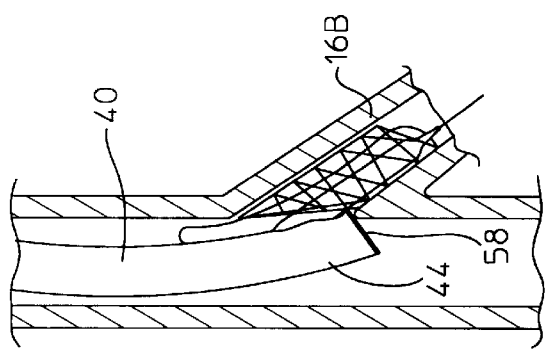
Figure 9B:
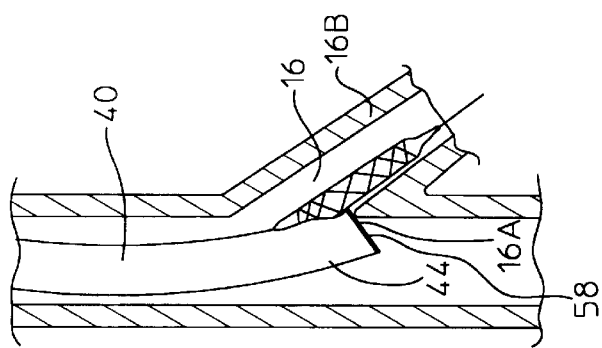
Figure 9A:
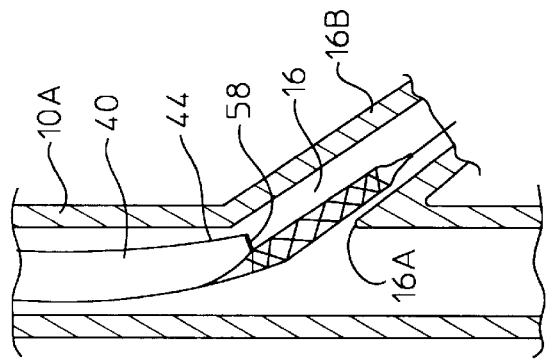

In the use of the stenting catheter of the present invention a bifurcation lesion is wired dilated with a conventional balloon dilatation catheter. An exchange is made for the stent deployment catheter. As shown in FIG. 9A, the distal end portion 44 of the stenting catheter 40 is advanced along a branching blood vessel 10A to a branching duct 16B having an ostium 16 with crux 16A. When the un-expanded stent and balloon are in the branching duct 16B, the catheter is turned as shown in FIG. 9B by the use of the torque control knob 50 to align the step-off 58 with the crux 16A at the bifurcation. The catheter assembly is then further advanced to bring the step-off into contact with the crux of the bifurcation. FIG. 9C shows deployment of the stent by inflating the balloon 64. FIG. 9D shows removal of the catheter and guide-wire.

Figure 7:
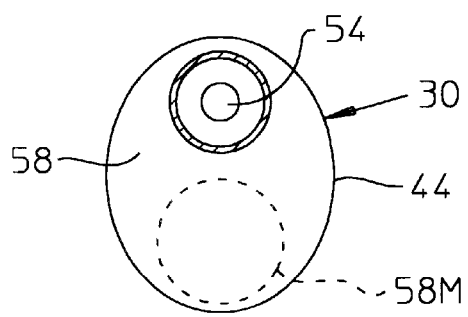
FIG. 7 is a view of the distal end taken along lines VII—VII of a catheter shown in FIG. 6.
Figure 8:
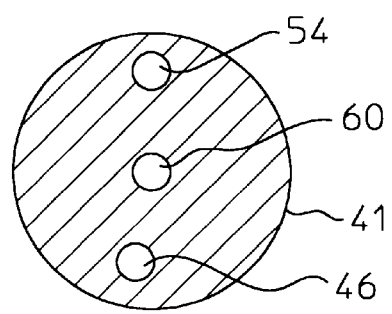
FIG. 8 is a sectional view taken along lines VIII—VIII of FIG. 6.
Figure 10:
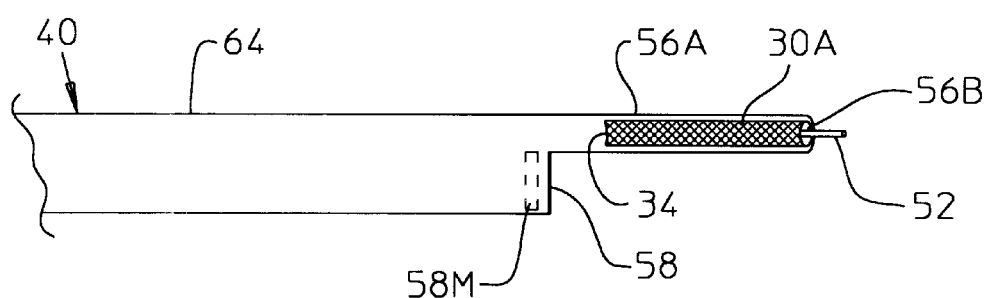
FIG. 10 is a partial view of a stenting catheter according to a second embodiment of the present invention.

Turning to FIG. 10, there is seen a second embodiment of the present invention which incorporates a self-expanding stent 30A having a beveled end 34. Self-expanding stents are known in the art and are made from a construction which expand upon the removal of the restraint. A second embodiment of a stenting catheter differs from the stenting catheter shown in FIGS. 5–7 and described hereinbefore by constructing the stent carrier in the form a sheathing 56A in which a self-expanding stent is housed during transportation to the deployment site in an branching anatomic duct. The self-expanding stent is carried on a sleeve 56B supported by the guide wire 52. The sheathing 56A is retractable to thereby remove the restraint and allow the self-expanding stent to deploy. The catheter 64 does not include a catheter balloon, balloon inflation lumen or a balloon inflation port. The steps of the preferred method of using the apparatus of FIG. 10 to deploy stent 30A are similar to the steps described with reference to the use of catheter 40 seen in FIGS. 9A–9D except that the step of expanding the stent by inflating the catheter balloon is replaced with the step of expanding stent 30A by retracting sheath 56A.

While the present invention has been described in connection with the preferred embodiments of the various figures, it is to be understood that other similar embodiments may be used or modifications and additions may be made to the described embodiments for performing the same function of the present invention without deviating therefrom. Therefore, the present invention should not be limited to any single embodiment, but rather construed in breadth and scope in accordance with the recitation of the appended claims.

What is claimed is:

1. A stent deployment catheter having a distal end portion containing a forward facing abutment surface laterally offset from a proximal end of a forward extending stent carrier having a length sufficient for supporting and deploying a stent to treat an ostial bifurcation lesion, said stent deployment catheter further having an actuator for angularly displacing said distal end portion in a body vessel to align said abutment surface with a common vessel wall at the crux of a vessel bifurcation and align said stent carrier along the site of the ostial bifurcation lesion.

2. The catheter according to claim 1 wherein said forward facing abutment surface is generally planar.

3. The catheter according to claim 1 wherein said stent carrier is eccentrically situated at one lateral side of said abutment surface.

4. The catheter according to claim 1 further including a radio opaque insert in said distal end portion generally coextensive with said forward facing abutment surface.

5. The catheter according to claim 1 wherein said actuator includes: a torque transmitting wire extending along said catheter; and a control knob for applying torque to an end portion of said torque transmitting wire at the proximal end of the catheter.

6. The catheter according to claim 1 wherein said stent carrier includes a catheter balloon for deploying a stent supported by the carrier.

7. The catheter according to claim 6 wherein said stent carrier includes a prolongation surface to the proximal end of said stent carrier and projecting along said distal end portion in a direction toward the proximal end of the catheter.

8. The catheter according to claim 1 wherein said stent carrier includes: a sheathing to contain a self-expanding stent; and a sleeve for supporting such a self expanding stent.

9. The catheter according to claim 1 further including a wire lumen extending along the length of a catheter body for guiding the distal end portion thereof to a stent deployment site.

10. The catheter according to claim 9 wherein said wire lumen internally traverses said forward extending stent carrier with an exit port at the distal end thereof.

11. A method for treating ostial bifurcation lesion, said method including the steps of:

advancing a stent laden carrier extending from a distal end portion of a catheter along a body vessel to a site of an ostial bifurcation lesion;

angularly displacing the stent laden carrier to orientate a stent carried thereby into a predetermined relation with the ostial bifurcation lesion established by concurrently bringing a forward facing abutment surface on the distal end portion of the catheter into a confronting relation with the crux of a vessel bifurcation at the site of the ostial bifurcation lesion; and deploying the stent from the stent laden carrier.

12. The method according to claim 11 wherein said angularly displacing includes rotating said stent carrier about a guide wire.

13. The method according to claim 11 including the further step of using a radio opaque insert to orientate said stent carrier into said predetermined relation.

14. The method according to claim 11 wherein said step of deploying a stent includes inflating a balloon catheter on which the stent is supported during said step of advancing.

15. The method according to claim 11 wherein said step of deploying the stent includes retracting a sheathing extending about a self-expanding-stent.

16. The method according to claim 11 including the further step of using a guide wire for directing said stent carrier into said predetermined relation.

* * * * *